United States Patent
McDowell et al.

(10) Patent No.: US 6,174,351 B1
(45) Date of Patent: Jan. 16, 2001

(54) PRESSURE MANAGEMENT AND VAPOR RECOVERY SYSTEM FOR FILLING STATIONS

(75) Inventors: Robert W. McDowell, San Diego; John M. Gray, San Marcos, both of CA (US)

(73) Assignee: Delaware Capital Formation, Inc., Wilmington, DE (US)

( * ) Notice: Under 35 U.S.C. 154(b), the term of this patent shall be extended for 0 days.

(21) Appl. No.: 09/277,334

(22) Filed: Mar. 26, 1999

(51) Int. Cl.⁷ ................................................ B01D 53/22
(52) U.S. Cl. ................................ 96/4; 096/111; 096/144; 095/50
(58) Field of Search .................... 95/8, 12, 19, 22, 95/45, 50, 146; 96/4, 7–10, 108, 111, 113, 130, 143, 144

(56) References Cited

U.S. PATENT DOCUMENTS

| | | | |
|---|---|---|---|
| 3,902,874 | * 9/1975 | McAndrew | 95/146 |
| 3,918,932 | * 11/1975 | Lee et al. | 95/146 X |
| 3,926,230 | * 12/1975 | Stary et al. | 95/146 X |
| 4,994,094 | 2/1991 | Behling et al. | 55/16 |
| 5,089,033 | 2/1992 | Wijmans | 55/16 |
| 5,092,911 | * 3/1992 | Williams et al. | 95/146 X |
| 5,199,962 | 4/1993 | Wijmans | 55/16 |
| 5,294,246 | * 3/1994 | Gardner, Sr. | 95/146 X |
| 5,464,466 | 11/1995 | Nanaji et al. | 95/45 |
| 5,484,000 | 1/1996 | Hasselmann | 141/7 |
| 5,537,911 | * 7/1996 | Ohlrogge et al. | 95/22 |
| 5,571,310 | * 11/1996 | Nanaji | 95/12 X |
| 5,611,841 | * 3/1997 | Baker et al. | 95/50 |
| 5,727,903 | * 3/1998 | Borray et al. | 95/50 X |
| 5,755,854 | * 5/1998 | Nanaji | 95/19 X |
| 5,843,212 | * 12/1998 | Nanaji | 95/12 X |
| B1 5,199,962 | 2/1995 | Wijmans | 95/39 |

FOREIGN PATENT DOCUMENTS

| | | | |
|---|---|---|---|
| 3824400 | * 1/1990 | (DE) | 95/50 |
| 3-109912 | * 5/1991 | (JP) | 95/8 |
| 1558446 | * 4/1990 | (SU) | 95/8 |

* cited by examiner

*Primary Examiner*—Robert H. Spitzer
(74) *Attorney, Agent, or Firm*—Dinsmore & Shohl LLP

(57) ABSTRACT

A vapor recovery and pressure management system for a vehicle refueling facility includes two rotary vane pumps and a hydrocarbon-stripping membrane between the pumps. One pump draws vapor from a storage tank as well as from refueling nozzles, while the other pump draws vapor from the membrane and discharges the vapor back into the tank. A controller controls both pumps to maintain a slight vacuum in the tank, thereby preventing leakage of hydrocarbons from the tank to the atmosphere. Clean air from the membrane is exhausted, preferably through a charcoal canister, and a hydrocarbon sensor monitors for the presence of undesirable hydrocarbons in the clean air exhaust. One or more liquid drop outs are provided for separating liquid from the hydrocarbon vapor and returning the liquid to the tank along with the vapor, preferably before the liquid is sent to the membrane, to thereby increase efficient fuel recovery and to protect the membrane from undesirable contact with liquid.

45 Claims, 3 Drawing Sheets

PRESSURE MANAGEMENT AND VAPOR RECOVERY SYSTEM FOR FILLING STATIONS

FIELD OF THE INVENTION

The present invention relates generally to filling stations, and more particularly to systems and methods for vapor recovery in filling stations and for managing pressure in storage tanks in filling stations.

BACKGROUND

As is familiar to drivers, filling stations typically enable people to dispense fuel from a storage tank (which can be buried underground) through nozzles that are inserted into the gas tanks of vehicles. As is also familiar, the nozzles often come equipped with boots, to trap otherwise polluting hydrocarbon vapors and thereby prevent the vapors from entering the atmosphere. The trapped vapors are then returned to the tank, i.e., are recovered, by a vapor recovery system. One such vapor recover system is disclosed in the present assignee's U.S. Pat. No. 5,484,000, incorporated herein by reference.

It happens that as vapor is returned to the tank, the pressure in the tank can become greater than atmospheric pressure. When this happens, pollutants can escape from the tank through small leaks. These leaks can be difficult to detect, particularly from underground storage tanks.

Accordingly, systems have been introduced to manage pressure in filling station storage tanks. One example of such a system is disclosed in Gilbarco's U.S. Pat. No. 5,464,466, incorporated herein by reference. In the Gilbarco system, a pump recirculates vapor from a storage tank through a membrane that separates clean air from hydrocarbon vapor, with clean air being exhausted to the atmosphere and hydrocarbon vapor being returned to the tank. The pump is operated to establish a desired pressure in the tank.

The present invention recognizes that several important improvements to the art can be made. First, the present invention recognizes that many commercial embodiments of pressure management systems require large, expensive compressors and/or vacuum pumps, some of which require three phase power. Three phase power, however, is not always readily available in many locations, and the size and expense of many pumps in use, and in particular positive displacement piston-type pumps, render such systems unduly complex and expensive to procure and maintain. As recognized herein, however, it is possible to provide a pressure management system that uses simple, inexpensive, yet effective pumps.

Another problem recognized by the present invention is that when membranes are used in existing systems, the membranes can be damaged by contact with liquid that might condense in the vapor lines. However, preventing formation of liquid in the vapor lines to promote membrane operation results in nothing but hydrocarbon vapor being returned to the storage tank. We have recognized that a disadvantage of returning only vapor to the storage tank is that the vapor is lost when the storage tank is accessed to refill the tank, an occurrence that can happen as frequently as twice a day in some locations. Understandably, filling stations operators would prefer to minimize the amount of fuel they lose as vapor, and environmentalists would likewise prefer to limit the amount of hydrocarbon vapors that escape from filling stations. Fortunately, we have recognized that is possible to both return liquid to storage tanks while preventing liquid from contacting membranes in the pressure management system.

Furthermore, we have recognized that is possible for membranes and other pressure management system components to fail, potentially leading to the release of hydrocarbons to the environment through the clean air exhaust line. Unfortunately, present systems do not seem to anticipate such failure and thus do not appear to provide for warning of such failure or for corrective action for such failure. We have recognized, however, that it is possible to address this shortcoming in an efficient and cost effective way.

SUMMARY OF THE INVENTION

A system is disclosed for managing pressure in a storage tank that contains hydrocarbons, with the system also returning vapor from fuel-dispensing nozzles that are in fluid communication with the tank. The system includes at least one vapor recovery system in fluid communication with the nozzles, and at least one pressure management system. The pressure management system includes at least one membrane that communicates with the vapor recovery system and the tank and that is arranged such that vapor from the vapor recovery system passes through the membrane before returning to the tank. The membrane separates hydrocarbon vapor from non-hydrocarbon vapor.

In a preferred embodiment, the pressure management system includes a clean air outlet and a hydrocarbon sensor communicating with the clean air outlet. Further, a charcoal canister can be in fluid communication with the clean air outlet to further cleanse air being discharged to the environment.

As disclosed in greater detail below, a pressure pump in the pressure management system has a suction in fluid communication with the tank and a discharge communicating with the membrane. A membrane assembly holds the membrane, and the membrane assembly communicates with the clean air outlet and a hydrocarbon outlet. A vacuum pump has a suction in communication with the hydrocarbon outlet and a discharge communicating with the tank.

The preferred pressure management system also includes at least one liquid drop out device communicating with the discharge of the pressure pump, the tank, and the membrane. If desired, a second liquid drop out device can be disposed in fluid communication with the discharge of the vacuum pump and the tank. A vapor blocker can be disposed between the first liquid drop out device and the tank for impeding vapor flow through the vapor blocker.

To manage pressure in the tank, a controller is electrically connected to at least one motor that actuates the pumps, and the controller selectively energizes the motor to establish a predetermined pressure range in the tank. When the charcoal canister mentioned above is provided, at least one solenoid valve communicates with the canister, and the controller selectively operates the valve or valves to establish forward air flow through the canister, wherein air from the membrane assembly flows through the canister to the clean air outlet. To backflush the canister, the controller operates the solenoid valve or valves to establish reverse air flow through the canister, wherein air flows through the canister to the tank to flush the canister.

In another aspect, a system is disclosed for managing pressure in a storage tank containing hydrocarbons. The system includes at least one pressure pump having a suction in communication with the tank, and the pressure pump also has a discharge. At least one membrane assembly includes at least one membrane communicating with the discharge of the pressure pump, with the membrane assembly also communicating with at least one clean air outlet and at least one hydrocarbon outlet. At least one vacuum pump has a suction in communication with the hydrocarbon outlet and a discharge communicating with the tank, and at least one hydrocarbon sensor is in fluid communication with the clean air outlet.

In still another aspect, a system for a vehicle refueling station having at least one storage tank and plural vehicle nozzles communicating therewith includes first and second rotary vane pumps. The first pump has a suction for receiving vapor from at least some of the nozzles. A membrane is between the pumps, and the membrane is in fluid communication with the pumps. At least one liquid drop out is in fluid communication with at least one of the pumps to reduce liquid contact with the membrane.

In yet another aspect, a pressure control system includes at least one membrane to control service station storage tank pressure. In accordance with the present invention, the system includes at least one clean air discharge of the membrane and at least one hydrocarbon sensor communicating with the clean air discharge for generating a failure signal when at least one predetermined concentration of hydrocarbons is present in the clean air discharge.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
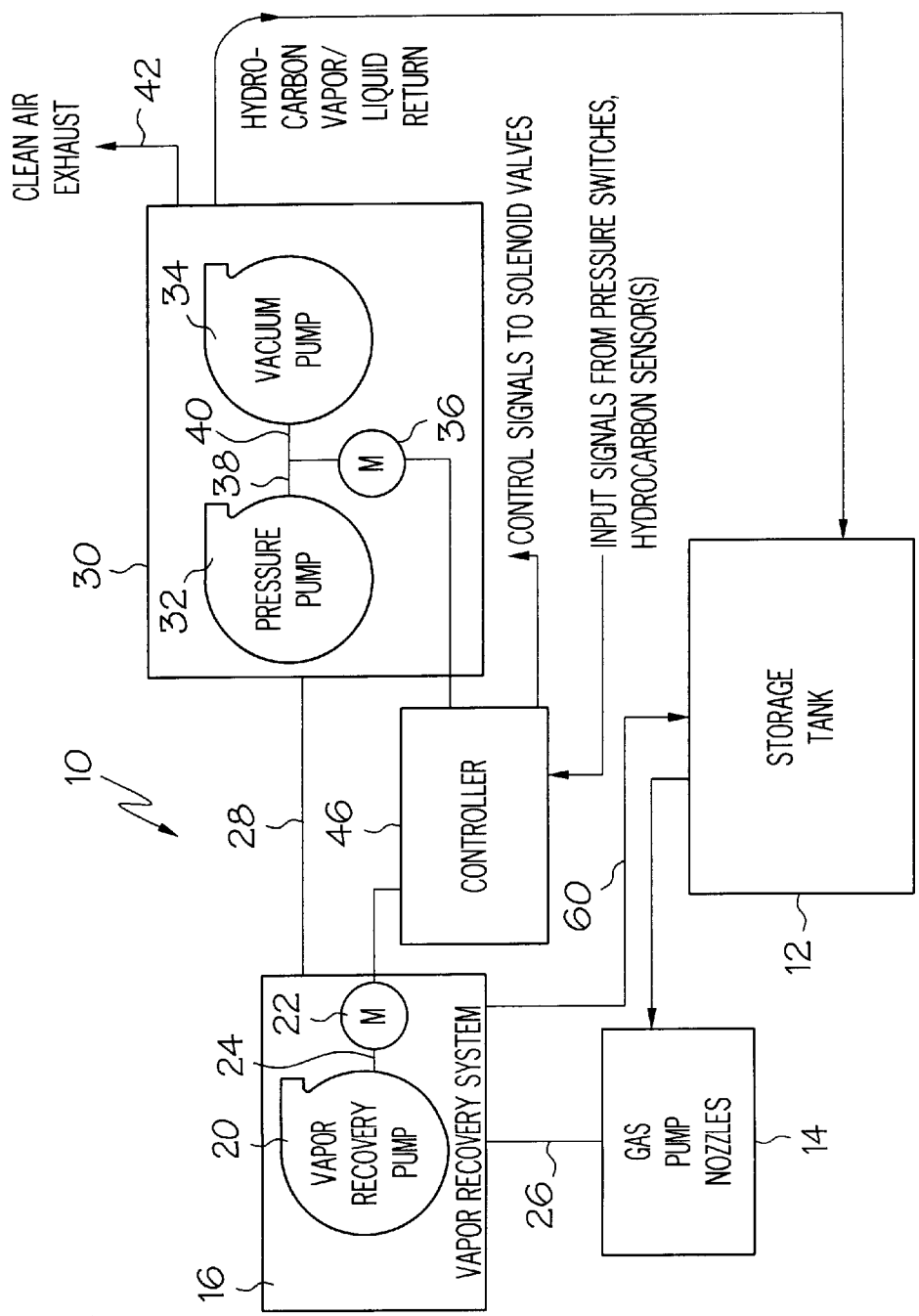
FIG. 1 is a high level block diagram of the present system.

Referring initially to FIG. 1, a system is shown and generally designated 10 for managing pressure in a storage tank 12 that contains hydrocarbons, specifically petroleum-based fuel, and for returning to the tank 12 vapor from fuel-dispensing nozzles 14 that are in communication with the tank 12. As shown, the system 10 includes a vapor recovery system 16 that is in communication with the nozzles 14. In one preferred embodiment, the vapor recovery system 16 includes a vapor recovery pump 20, also referred to as a "blower", that is actuated by an electric, preferably single phase motor 22, to which the pump 20 is coupled via a coupling represented by the line 24. The vapor recovery pump can be a type GVR 313 pump made by Rotron. Also, the vapor recovery pump 20 is in fluid communication with the nozzles 14 via a fluid line 26. Most vapor collected from the vehicle fuel tanks is returned to the tank 12 via a tank suction line 60, described in further detail below. Excess vapor, on the other hand, is sent from the vapor recovery system 16 via a fluid line 28 to a pressure management system 30, also described in further detail. As described below, the pressure management system 30 includes a membrane, not shown in FIG. 1 for clarity of disclosure but shown in FIG. 2.

The pressure management system 30 preferably includes a pressure pump 32, also referred to as a "compressor", and a vacuum pump 34. In the preferred embodiment, both the pressure pump 32 and vacuum pump 34 are identical type E10 rotary vane pumps made by Blackmer, and both pumps 32, 34 are actuated by one single phase ac two horsepower motor 36. In FIG. 1, the couplings between the motor 36 and pumps 32, 34 are represented by the lines 38, 40, respectively. The couplings can be belt drive mechanisms known in the art.

As described further below, the pressure and vacuum pumps 32, 34 respectively push and pull vapor through a membrane that separates clean air from hydrocarbon vapor. The clean air is exhausted to atmosphere through a clean air outlet 42, whereas the hydrocarbon vapor is returned to the tank 12 through a hydrocarbon return line 44. With the above introductory disclosure in mind, the skilled artisan will appreciate that excess vapor from the vapor recovery system 16 passes through the membrane in the pressure management system 30 before returning to the tank 12.

As also discussed further below, the pressure management system 30 can include one or more solenoid valves and one or more sensors, and the pump motors 22, 36 and solenoid valves are electrically connected to a controller 46. In accordance with the detailed discussion below, the controller 46 is responsive to the system sensors for selectively energizing the motor 22 and for selectively actuating the solenoid valves. In one preferred embodiment, the controller 46 is implemented by discrete logic on a circuit board for undertaking the sequence of operations described below. It is to be understood, however, that the controller 46 can be a PC or other computer that is programmed with a software application to undertake the present logic.

Figure 2:
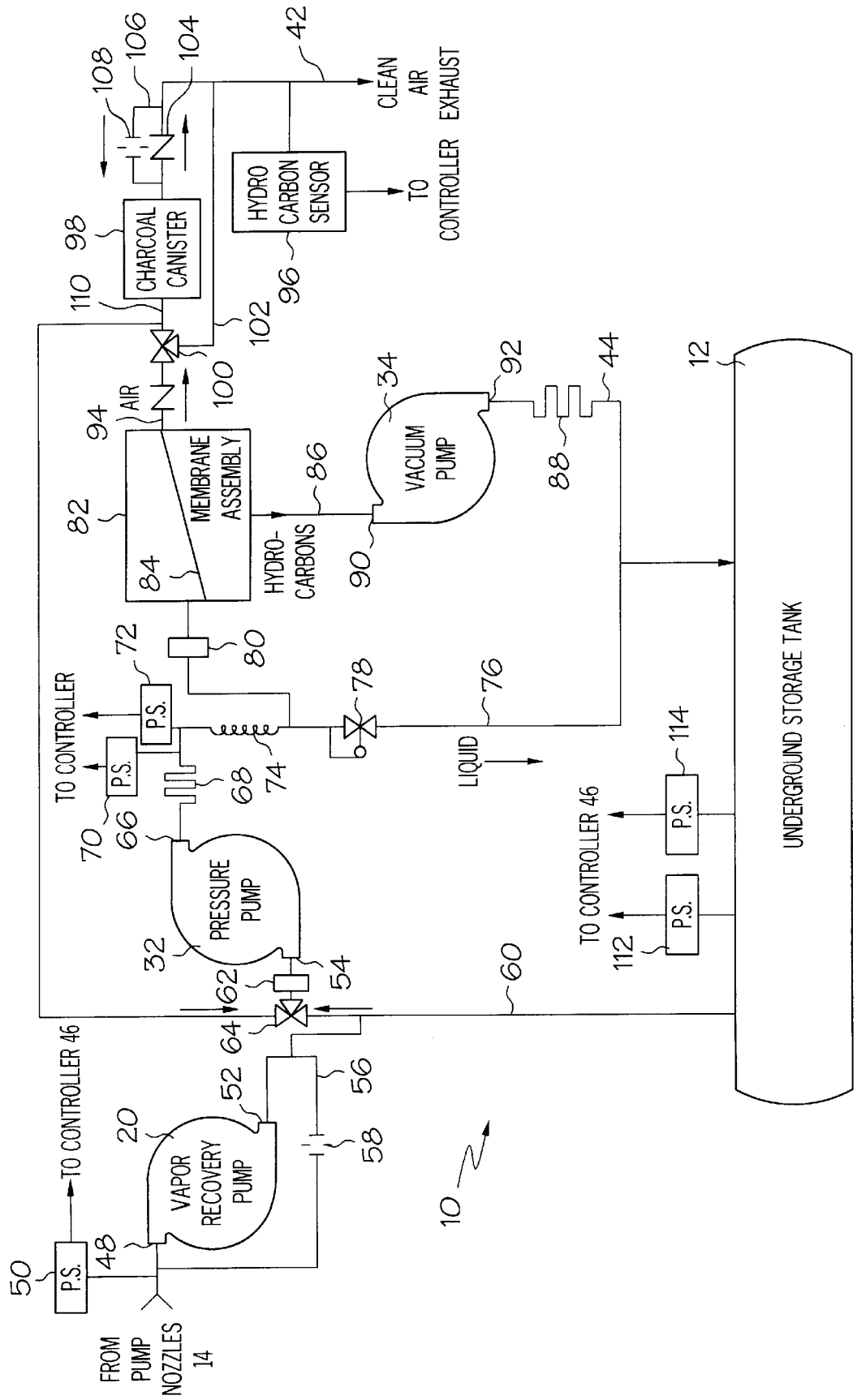
FIG. 2 is a schematic piping diagram of the system.

Now referring to FIG. 2, in which fluid flow direction is indicated by various arrows, the vapor recovery pump 20 has a suction port 48 that communicates with the nozzles 14 to evacuate hydrocarbon vapor away from the nozzles 14. A vapor recovery pressure switch or sensor 50 communicates with the suction port 48 of the vapor recovery pump 20 for generating an electrical signal that is sent to the controller 46. The electrical signal is representative of the pressure at the suction port 48 of the vapor recovery pump 20. When the signal indicates that the vapor recovery pump 20 is not functioning (e.g., when no vacuum exists at the suction 48), the controller 46 stops the motors 22, 36 and, if desired, activates an audible or visual alarm.

Hydrocarbon vapor is discharged through a discharge port 52 of the vapor recovery pump 20. As shown in FIG. 2, the discharge port 52 of the vapor recovery pump 20 communicates with a suction port 54 of the pressure pump 32. Additionally, a bypass line 56 establishes a separate path for fluid communication from near the suction port 48 of the vapor recovery pump 20 to near the discharge port 52 of the pump 20, and a bypass element 58 partially occludes the bypass line 56. In one preferred embodiment, the bypass element 58 is established by a vacuum regulator that includes a vertical pipe having a weight movably disposed therein, with the weight being movable to a closed position in which fluid communication through the bypass line 56 is blocked. When the vacuum at the suction port 48 of the vapor recovery pump 20 becomes sufficiently large, the weight lifts and allows vapor from the discharge port 52 to bypass the pump 20 and recirculate back to the suction port 48. Alternatively, the element 58 can be established by an orifice plate having two quarter-inch diameter holes formed therein. In any case, the bypass element 58 is configured as appropriate to establish a desired constant air to liquid flow rate ratio (A/L) to promote efficient and effective operation of the membrane of the present invention.

Continuing with the description of the preferred piping system shown in FIG. 2, a tank suction line 60 establishes a path for fluid communication from the tank 12 to the suction 54 of the pressure pump 32 as shown. If desired, a tank suction line particulate filter 62 can be disposed in the suction line of the pressure pump 32 to filter particles out of the vapor from the tank 12 that is evacuated by the pressure pump 32. In one preferred embodiment, the tank suction line particulate filter 62 is a particulate filter made by Cim-Tek Filtration. Also, for purposes to be shortly disclosed, a tank suction line three-way solenoid valve 64 is disposed in the tank suction line 60, it being understood that the valve 64 is electrically connected to the controller 46. During normal operation, the tank suction valve 64 is configured to establish communication between the suction line 60 and the pressure pump 32, whereas during the below-described backflush procedure the suction valve 64 is configured to establish communication between the pressure pump 32 and a backflush return line 65.

The pressure pump 32 discharges fluid through a discharge port 66 to a condenser 68. The condenser 68 condenses vapor in the discharge of the pressure pump 32 to liquid. As envisioned herein, the condenser 68 can be implemented by a conventional heat exchanger such as an air cooler/radiator. Alternatively, we have found that the condenser 68 can be established by an uninsulated segment of the piping line, or indeed by a length of rubber tubing that can be disposed in the piping line.

High and low safety shut off pressure switches 70, 72 communicate with the discharge 66 of the pressure pump 32 for detecting the discharge pressure thereof. In one presently preferred embodiment, when the discharge pressure drops below 15 psig, the low pressure switch 72 generates a low pressure signal, and the signal is sent to the controller 46 to activate an alarm and/or to deenergize the pumps of the present invention. In contrast, when the discharge pressure exceeds 25 psig, the high pressure switch 70 generates a high pressure signal, and the signal is sent to the controller 46 to activate an alarm and/or to deenergize the pumps of the present invention.

Fluid from the condenser 68 flows through a liquid drop out device 74, as shown in FIG. 2. As intended by the present invention, the liquid drop out device 74 separates liquid in the fluid from vapor, with the liquid passing through a liquid return line 76 to the tank 12. In one preferred embodiment, the liquid drop out device 74 is a type SEP 10 or 25 cyclone separator. Other equivalent devices, however, can be used in lieu of a cyclone separator, including a drop out pot, a dryer, a small diameter pipe to large diameter pipe transition that turns vertical, stainless steel wool or batting, or a combination of one or more of such devices.

A vapor blocker, such as pressure activated valve or float switch 78, can be disposed in the liquid return line 76 to impede vapor from passing through the liquid return line 76. Other equivalent vapor-blocking devices can be used in lieu of the pressure activated valve or float switch 78, such as, e.g., a float drain check valve, an orifice, or a poppet-implemented drain trap.

In contrast to the path that liquid takes from the liquid drop out device 74, vapor passes through a particulate filter 80 to a membrane assembly 82. A membrane, represented by the line 84 in FIG. 2, separates hydrocarbon vapor from clean air. It may now be appreciated that the liquid drop out device 74 not only advantageously returns, as liquid, some of vapor from the nozzles 14, but also reduces or eliminates liquid contact with the membrane 84, which would otherwise be deleterious to the performance of the membrane 84.

In the preferred embodiment, the membrane 84 is made by Membrane Technology and Research (MTR) of Menlo Park, Calif., model #340-4120LPI. Other membranes can be used, including those in U.S. Pat. Nos. 5,199,962 and 5,089,033, incorporated herein by reference.

As can be readily appreciated in reference to FIG. 2, after passing through the membrane 84 the hydrocarbon vapor is evacuated through a hydrocarbon outlet line 86 from the membrane assembly 82 by the vacuum pump 34, which pumps the vapor back to the tank 12 via the hydrocarbon return line 44. If desired, the hydrocarbon return line 44 can join the return line 76 as shown, to minimize openings into the tank 12. Also, if desired a second condenser 88 or a second liquid drop out device can be disposed in the hydrocarbon return line 44 to further separate liquid from vapor and thereby increase the amount of hydrocarbons in the liquid phase that are returned to the tank 12. In any case, a suction port 90 of the vacuum pump 34 is in communication with the hydrocarbon outlet of the membrane assembly 82, while a discharge port 92 of the vacuum pump 34 communicates with the tank 12.

Having described the vapor and liquid hydrocarbon return paths to the tank 12, attention is now directed to the clean air exhaust path. As shown in FIG. 2, clean air from the membrane assembly 82 is exhausted through a clean air check valve 94 and the clean air exhaust 10 line 42 to atmosphere. To ensure that the clean air being exhausted to the environment does not contain an amount of hydrocarbon vapor that exceeds regulatory limits, a hydrocarbon sensor 96 communicates with the clean air exhaust 42, and the hydrocarbon sensor 96 generates a signal that is sent via an electrical line or wireless network to the controller 46 (FIG. 1), which deenergizes the motors 22, 36 when a hydrocarbon limit is reached.

To further cleanse hydrocarbons from the air that is exhausted to the environment, a charcoal canister 98 can be disposed between the membrane assembly 82 and clean air exhaust 42 as shown. As the air passes through the canister 98, hydrocarbons are removed from the air.

When the charcoal canister is provided, the present invention recognizes that it might be desirable to backflush the canister from time to time, to refresh the activated material in the canister. To facilitate this, a three-way solenoid backflush valve 100 that is controlled by the controller 46 is disposed in the clean air outlet line upstream of the charcoal canister 98. During normal operation, the backflush valve 100 is configured to establish communication between the membrane assembly 82 and the charcoal canister 98. During backflush, however, the backflush valve 100 is configured to establish communication between the membrane assembly 82 and a 25 backflush line 102. A canister discharge check valve 104 is disposed downstream of the charcoal canister 98 in the clean air exhaust line 42, and a check valve bypass line 106 interconnects the upstream and downstream sides of the check valve 104 as shown. An orifice 108 is disposed in the bypass line 106 to establish a backflush flow rate.

In normal operation of the system 10, forward air flow is established through the canister 98, wherein air from the membrane assembly 82 flows through the canister 98 to the clean air outlet 42. When the controller 46 determines that the canister 98 should be backflushed based on, e.g., the elapse of a predetermined time period between backflushes, or a high hydrocarbon signal from the hydrocarbon sensor 96, or based on other criteria including a manually input "backflush" command signal, the controller 46 establishes a backflush configuration of the system 10. To do this, the controller 46 signals the tank suction valve 64 to establish communication between the suction 54 of the pressure pump 32 and the backflush return line 65. Also, the controller 46 signals the backflush valve 100 to establish communication between the charcoal canister 98 and the backflush line 102.

In the backflush configuration, the pressure pump 32 takes a suction through the backflush return line 65 on the inlet side 110 of the canister 98. The discharge of the pressure pump 32 flows through the membrane 84 as described before, but instead of passing in the normal direction through the canister 98, the air is directed by the backflush valve 100 into the backflush line 102. From the backflush line 102, air passes through the bypass line 106 and then passes through the canister 98 in the reverse direction, thereby flushing the canister 98. As mentioned above, the contaminated backflush air is then drawn through the backflush return line 65 into the pressure pump 32, and discharged into the membrane assembly 82 to clean the air. When backflushing is complete, the controller 46 reconfigures the three way valves 64, 100 for normal operation. To avoid overpressurizing the storage tank 12, backflushing can be undertaken incrementally by cycling the system 10 between the backflush configuration (to cleanse the canister 98) and normal configurations (to reduce pressure in the tank 12) several times, e.g., twenty times, until the canister 98 has been completely backflushed.

Completing the description of FIG. 2, on and off pressure switches 112, 114 communicate with the tank 12 for generating respective pressure signals. In the preferred embodiment, the on pressure switch 112 generates a signal when the tank 12 internal pressure is between 0.1" W.C. and 1.0" W.C. (i.e., when the tank 12 has a slight internal overpressure). In contrast, the off pressure switch 114 generates a signal when the tank 12 internal pressure is between −0.5" W.C. and −1.0" W.C. (i.e., when the tank 12 has a slight internal vacuum). These signals are sent to the controller 46, which energizes the motor 36 upon receipt of an "on" signal from the on pressure switch 112 and which deenergizes the motor 36 upon receipt of an "off" signal from the off pressure switch 114.

Figure 3:
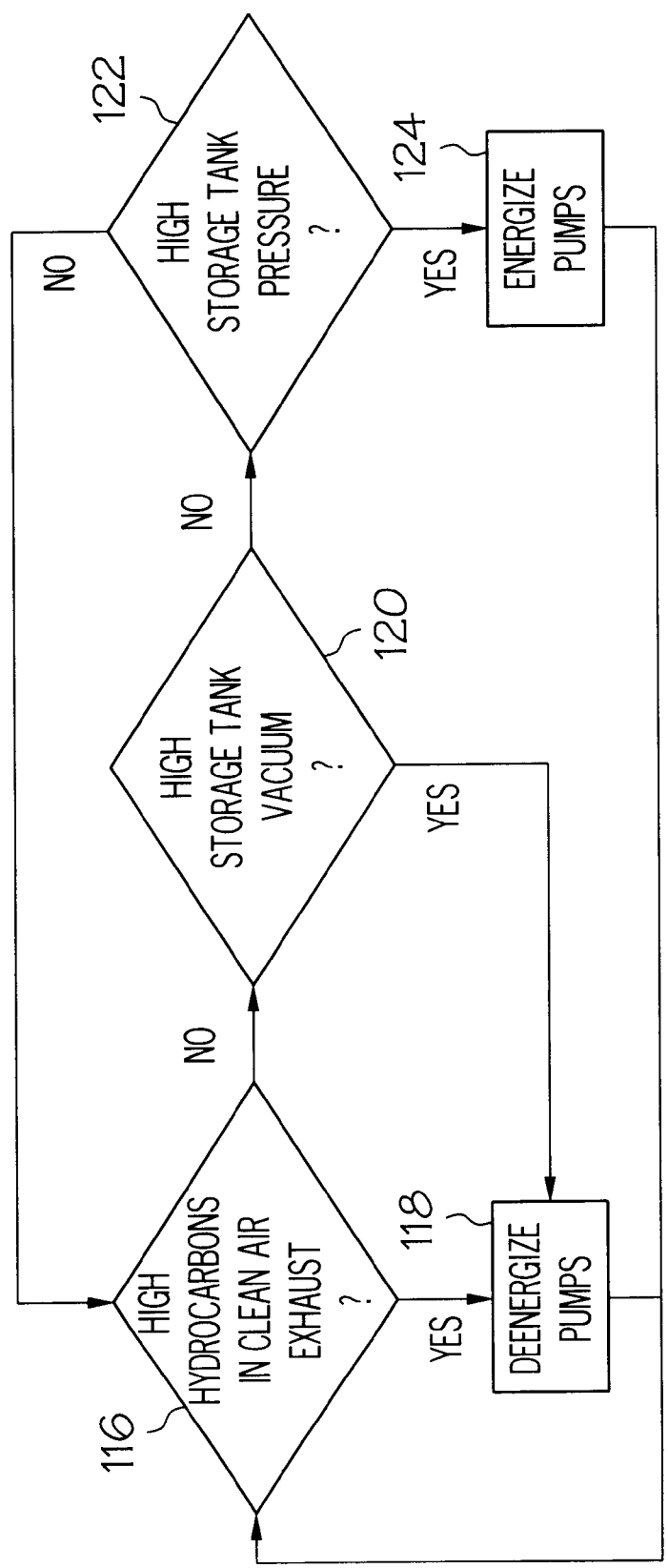
FIG. 3 is a flow chart showing the pump control logic.

The above-described logic (omitting charcoal canister backflush operations for clarity) can be further appreciated in reference to FIG. 3, which shows the logic in flow format for disclosure purposes. It is to be understood that the logic can also be thought of in terms of state logic.

Commencing at decision diamond 116, the controller 46 determines whether the hydrocarbon level in the clean air exhaust is high, as indicated by the signal from the hydrocarbon sensor 90. If it is, the controller 46 deactivates one or more of the pumps of the present invention at block 118. In the preferred embodiment, the pumps must be manually reset to resume normal operation. Otherwise, i.e., if the test at decision diamond 116 is negative, the logic moves to decision diamond 120, wherein the controller 46 determines whether the vacuum in the tank 12 is high. If it is, the logic moves to block 118, but otherwise proceeds to decision diamond 122 to determine whether the pressure in the tank 12 is high. A negative test result causes the logic to loop back to decision diamond 116. In contrast, a positive test result at decision diamond 122 causes the controller 46 to activate the pumps at block 124. As indicated above, however, the present logic need not flow from decision diamond to decision diamond, but instead can assume "on" and "off" states and await the various signals described herein to change state appropriately. In any case, the controller selectively energizes the pump motor 36 to establish a predetermined pressure range in the tank 12.

While the particular PRESSURE MANAGEMENT AND VAPOR RECOVERY SYSTEM FOR FILLING STATIONS as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. For example, multiple two-way solenoid valves can be used in lieu of each three-way solenoid valve where appropriate, or a single pressure sensor can be used in lieu of two pressure switches where appropriate. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for".

What is claimed is:

1. A system for collecting vapor from a nozzle, and for managing pressure in a storage tank capable of communicating with the nozzle and capable of containing hydrocarbons, comprising:
   at least one vapor recovery system capable of communicating with the nozzle; and
   at least one pressure management system including at least one membrane capable of communicating with the vapor recovery system and the tank, and being arranged such that at least some vapor from the vapor recovery system can pass through the membrane before returning to the tank, the membrane substantially separating a hydrocarbon portion of the vapor from a non-hydrocarbon portion of the vapor.

2. The system of claim 1, wherein the pressure management system includes a clean air outlet and a hydrocarbon sensor communicating with the clean air outlet.

3. The system of claim 2, further comprising at least one charcoal canister communicating with the clean air outlet.

4. The system of claim 3, further comprising at least one solenoid valve communicating with the canister and at least one controller electrically connected to the at least one solenoid valve, the controller selectively operating the at least one solenoid valve to establish forward air flow through the canister, wherein air from the membrane assembly flows through the canister to the clean air outlet, the controller also selectively operating the at least one solenoid valve to establish reverse air flow through the canister, wherein air flows through the canister to the tank to flush the canister.

5. The system of claim 1, wherein the pressure management system further includes:
   at least one pressure pump having a suction capable of communicating with the tank and the vapor recovery system, and a discharge capable of communicating with the membrane;
   at least one membrane assembly holding the membrane, the membrane assembly capable of communicating with at least one hydrocarbon outlet; and
   at least one vacuum pump having a suction capable of communicating with the hydrocarbon outlet and a discharge capable of communicating with the tank.

6. The system of claim 5, wherein the pressure management system includes at least one liquid drop out device.

7. The system of claim 6, wherein the liquid drop out device is a first liquid drop out device, and the first liquid drop out device communicates with the discharge of the pressure pump, the tank, and the membrane.

8. The system of claim 7, further comprising a second liquid drop out device communicating with the discharge of the vacuum pump and the tank.

9. The system of claim 7, further comprising at least one vapor blocker communicating with the first liquid drop out device and the tank for impeding vapor flow through the vapor blocker.

10. The system of claim 6, wherein the liquid drop out device is a second liquid drop out device, and the second liquid drop out device communicates with the discharge of the vacuum pump and the tank.

11. The system of claim 5, further comprising a controller electrically connected to at least one motor, the motor being coupled to both of the pumps, the controller selectively energizing the motor to establish a predetermined pressure range in the tank.

12. The system of claim 11, wherein the vapor recovery system comprises a vapor recovery pump, and wherein the controller is electrically connected to a second motor coupled to the vapor recovery pump.

13. The system of claim 5, wherein both pumps are rotary vane pumps.

14. The system of claim 5, wherein the vapor recovery system comprises a vapor recovery pump having a discharge capable of communicating with the suction of the pressure pump.

15. The system of claim 1, wherein the at least one vapor recovery system comprises a vapor recovery pump capable of communicating with the nozzle.

16. The system of claim 1, further comprising a tank line and a return line, wherein the vapor recovery system is capable of communicating with the pressure management system via the tank line, the tank is capable of communicating with the pressure management system via the tank line, and the pressure management system is capable of communicating with the tank via the return line.

17. A system for managing pressure in a storage tank capable of containing hydrocarbons and capable of communicating with a vapor recovery system, comprising:
   at least one pressure pump having a suction capable of communicating with the tank and the vapor recovery system, the pressure pump having a discharge;
   at least one membrane assembly including at least one membrane capable of communicating with the discharge of the pressure pump, the membrane assembly being capable of communicating with at least one hydrocarbon outlet; and
   at least one vacuum pump having a suction capable of communicating with the hydrocarbon outlet, the vacuum pump having a discharge capable of communicating with the tank.

18. The system of claim 17, further comprising at least one liquid drop out device.

19. The system of claim 18, wherein the liquid drop out device is a first liquid drop out device, and the first liquid drop out device communicates with the discharge of the pressure pump, the tank, and the membrane.

20. The system of claim 19, further comprising a second liquid drop out device communicating with the discharge of the vacuum pump and the tank.

21. The system of claim 19, further comprising at least one vapor blocker communicating with the first liquid drop out device and the tank for impeding vapor flow through the vapor blocker.

22. The system of claim 17, further comprising a controller electrically connected to at least one motor, the motor being coupled to both of the pumps, the controller selectively energizing the motor to establish a predetermined pressure range in the tank.

23. The system of claim 22, wherein the vapor recovery system comprises a vapor recovery pump, and wherein the controller is electrically connected to a second motor coupled to the vapor recovery pump.

24. The system of claim 17, wherein both pumps are rotary vane pumps.

25. The system of claim 17, wherein the vapor recovery system comprises a vapor recovery pump having a discharge capable of communicating with the suction of the pressure pump.

26. The system of claim 17, further comprising a hydrocarbon sensor capable of communicating with a clean air outlet of the membrane assembly.

27. The system of claim 26, further comprising at least one charcoal canister communicating with the clean air outlet.

28. The system of claim 27, further comprising at least one solenoid valve communicating with the canister and electrically connected to the controller, the controller selectively operating the at least one solenoid valve to establish forward air flow through the canister, wherein air from the membrane assembly flows through the canister to the clean air outlet, the controller also selectively operating the at least one solenoid valve to establish reverse air flow through the canister, wherein air flows through the canister to the tank to flush the canister.

29. The system of claim 17, further comprising a tank line and a return line, wherein the vapor recovery system is capable of communicating with the suction of the pressure pump via the tank line, the tank is capable of communicating with the suction of the pressure pump via the tank line, and the discharge of the vacuum pump is capable of communicating with the tank via the return line.

30. A system for a vehicle refueling station having at least one storage tank and a nozzle capable of communicating therewith, comprising:
   first and second pumps, the first pump having a suction capable of communicating vapor from the nozzle and vapor from the tank; and
   a membrane between the pumps and capable of communicating therewith.

31. The system of claim 30, further comprising at least one clean air outlet communicating with the membrane for exhausting air therethrough and at least one hydrocarbon sensor communicating with the clean air outlet.

32. The system of claim 30, further comprising at least one motor coupled to both pumps.

33. The system of claim 32, wherein the motor comprises a single phase motor.

34. The system of claim 30, wherein the pumps comprise rotary vane pumps.

35. The system of claim 30, further comprising a vapor recovery system capable of communicating vapor from the nozzle to the tank and the first pump.

36. The system of claim 30, further comprising a liquid drop out communicating with at least one of the pumps and adapted to reduce liquid contact with the membrane.

37. A pressure control system for a storage tank capable of receiving vapor via a vapor recovery system, comprising:
   a membrane configured to control storage tank pressure and capable of receiving vapor from both the storage tank and the vapor recovery system, the membrane including at least one clean air discharge; and at least one hydrocarbon sensor capable of communicating with the clean air discharge and adapted to generate a signal when at least one predetermined concentration of hydrocarbons is present in the clean air discharge.

38. The system of claim 37, further comprising at least one condenser in the system.

39. The system of claim 38, further comprising at least one liquid drop out device in the system.

40. The system of claim 37, further comprising at least one charcoal canister in the clean air discharge to remove hydrocarbons therefrom.

41. The system of claim 40, further comprising one or more valves configurable to backflush the charcoal canister.

42. The system of claim 41, further comprising at least one condenser in the system.

43. The system of claim 40, further comprising at least one condenser in the system.

44. A system for controlling hydrocarbon emissions from a fuel dispensing facility comprising:

a tank;

a nozzle capable of communicating with the tank;

a vapor recovery system capable of communicating with the nozzle; and a pressure management system including a membrane capable of communicating with the vapor recovery system and the tank, and being arranged such that at least some vapor from the vapor recovery system can pass through the membrane before returning to the tank, the membrane substantially separating a hydrocarbon portion of the vapor from a non-hydrocarbon portion of the vapor.

45. The system of claim 44, wherein the vapor recovery system comprises a vapor recovery pump having a discharge capable of communicating with the pressure management system and the tank.

* * * * *